US00H002261H

(19) United States
(12) Statutory Invention Registration
Simmons, Jr.

(10) Reg. No.: US H2261 H
(43) Published: Aug. 2, 2011

(54) DISC AND FACET REPLACEMENT

(76) Inventor: James W. Simmons, Jr., San Antonio, TX (US)

(21) Appl. No.: 11/528,023

(22) Filed: Sep. 26, 2006

Related U.S. Application Data

(60) Provisional application No. 60/720,414, filed on Sep. 26, 2005.

(51) Int. Cl.
*A61F 2/44* (2006.01)

(52) U.S. Cl. ..... 623/17.11

(58) Field of Classification Search ..... 623/17.11–17.16
See application file for complete search history.

(56) References Cited

U.S. PATENT DOCUMENTS

| | | | | | |
|---|---|---|---|---|---|
| 6,733,533 | B1 | | 5/2004 | Lozier | 623/17.12 |
| 7,214,243 | B2 | * | 5/2007 | Taylor | 623/17.11 |
| 7,323,011 | B2 | * | 1/2008 | Shepard et al. | 623/17.11 |
| 7,601,173 | B2 | * | 10/2009 | Messerli et al. | 623/17.11 |
| 2002/0029084 | A1 | * | 3/2002 | Paul et al. | 623/23.63 |
| 2002/0099444 | A1 | * | 7/2002 | Boyd et al. | 623/17.16 |
| 2003/0204261 | A1 | * | 10/2003 | Eisermann et al. | 623/17.14 |
| 2004/0024460 | A1 | * | 2/2004 | Ferree | 623/17.12 |
| 2004/0093082 | A1 | * | 5/2004 | Ferree | 623/17.11 |
| 2004/0186577 | A1 | * | 9/2004 | Ferree | 623/17.16 |
| 2004/0254644 | A1 | * | 12/2004 | Taylor | 623/17.13 |
| 2005/0033439 | A1 | | 2/2005 | Gordon et al. | 623/17.16 |
| 2005/0154461 | A1 | | 7/2005 | Humphreys et al. | 623/17.11 |
| 2005/0154466 | A1 | | 7/2005 | Humphreys et al. | 623/17.16 |
| 2005/0165487 | A1 | | 7/2005 | Muhanna et al. | 623/17.15 |
| 2005/0171610 | A1 | | 8/2005 | Humphreys et al. | 623/17.15 |
| 2005/0187633 | A1 | * | 8/2005 | Ferree | 623/17.15 |
| 2005/0192674 | A1 | * | 9/2005 | Ferree | 623/17.13 |
| 2005/0277930 | A1 | | 12/2005 | Parsons | 606/61 |
| 2006/0004454 | A1 | * | 1/2006 | Ferree et al. | 623/17.15 |
| 2006/0052785 | A1 | | 3/2006 | Augostino et al. | 606/61 |
| 2006/0052870 | A1 | * | 3/2006 | Ferree | 623/17.11 |
| 2006/0190084 | A1 | * | 8/2006 | Doubler et al. | 623/17.14 |
| 2006/0247778 | A1 | * | 11/2006 | Feree et al. | 623/17.14 |

* cited by examiner

*Primary Examiner*—Dan Pihulic
(74) *Attorney, Agent, or Firm*—Wayne J. Colton, Inc.

(57) ABSTRACT

An artificial disc for replacement of a spinal three-joint complex of a mammal includes a generally spinal disc-shaped upper plate having an anterior section and a posterior section and a generally spinal disc-shaped lower plate also having an anterior section and a posterior section. The anterior section of the upper plate is selectively separable from the posterior section of the upper plate and the anterior section of the lower plate is likewise selectively separable from the posterior section of the lower plate. A ball is interposed the lower face of the upper plate and the upper face of the lower plate and a plurality of posts, each projecting from one of the faces toward the other of the faces corresponds to a plurality of detents provided on the one of the faces opposite the face from which the corresponding post projects for engaging the posts.

10 Claims, 9 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DISC AND FACET REPLACEMENT

RELATED APPLICATION

This present application claims all available benefit under 35 U.S.C. § 119(e) of co-pending U.S. provisional patent application Ser. No. 60/720,414 filed Sep. 26, 2005. By this reference, the entire disclosure of U.S. provisional patent application Ser. No. 60/720,414, including the drawings, is incorporated herein as though now set forth in its entirety.

FIELD OF THE INVENTION

The present invention relates to medical devices. More particularly, the invention relates to an artificial intervertebral disc and facet replacement that very closely approximates the function of a natural three-joint disc and facet complex and that may be placed or extracted from or to either the anterior or posterior of a patient under treatment as may be medically determined to be appropriate and, in the case of extraction, without regard for whether the disc and facet replacement was placed from the anterior or posterior.

BACKGROUND OF THE INVENTION

Deterioration through disease or damage from injury often necessitates that a patient undergo surgical intervention for the removal of his or her natural three-joint disc and facet complex and replacement thereof with an artificial disc. Unfortunately, the available artificial discs do not generally well approximate the function of a natural three-joint disc and facet complex. Still further, the available artificial discs cannot generally be placed or extracted from or to either the anterior or posterior of a patient under treatment as may be medically determined to be appropriate and, in the case of extraction, without regard for whether the artificial disc was placed from the anterior or posterior.

With the shortcomings of the prior art in mind, it is therefore an principal object of the present invention to improve over the prior art by providing an artificial disc and facet replacement that may be placed or extracted from or to either the anterior or posterior of a patient under treatment as may be medically determined to be appropriate and, in the case of extraction, without regard for whether the disc and facet replacement was placed from the anterior or posterior. Additionally, it is an object of the present invention to provide such an artificial disc and facet replacement that also very closely approximates the function of a natural three-joint disc and facet complex.

SUMMARY OF THE INVENTION

In accordance with the foregoing objects, the present invention—an artificial disc for replacement of a spinal three-joint complex of a mammal—generally comprises a generally spinal disc-shaped upper plate comprising an anterior section and a posterior section and a generally spinal disc-shaped lower plate also comprising an anterior section and a posterior section. The anterior section of the upper plate is selectively separable from the posterior section of the upper plate and the anterior section of the lower plate is likewise selectively separable from the posterior section of the lower plate. A ball is interposed the lower face of the upper plate and the upper face of the lower plate and a plurality of posts, each projecting from one of the faces toward the other of the faces corresponds to a plurality of detents provided on the one of the faces opposite the face from which the corresponding post projects for engaging the posts.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto. As used herein, reference to an anatomical coordinate such as, for example, anterior, posterior, superior, inferior, sagittal plane, axial plane and the like, should be given its ordinary meaning with respect to human anatomy and, when applied to the disc and facet replacement 20 of the present invention and/or components thereof should be considered as describing the disc and facet replacement 20 as operably positioned as particularly shown in FIGS. 11 and 12. Accordingly, within this frame of reference, reference to the terms "upper" and/or "lower" should be taken as reference to components generally superior and/or inferior, respectively.

Figure 1A:
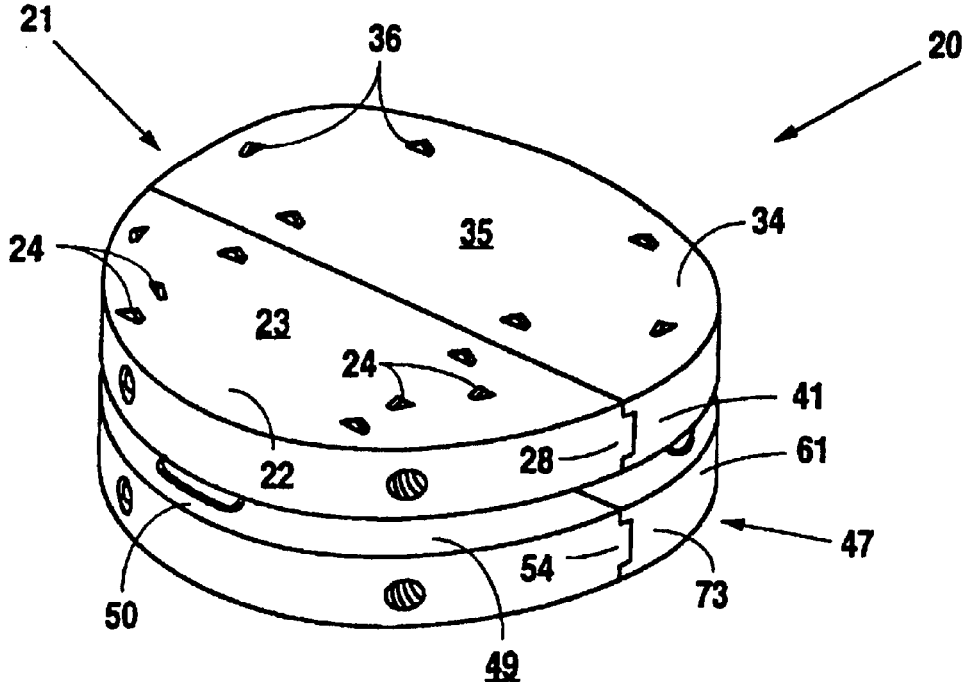
FIG. 1A shows, in a superior perspective view, the preferred embodiment of the assembled disc and facet replacement of the present invention.
Figure 1B:
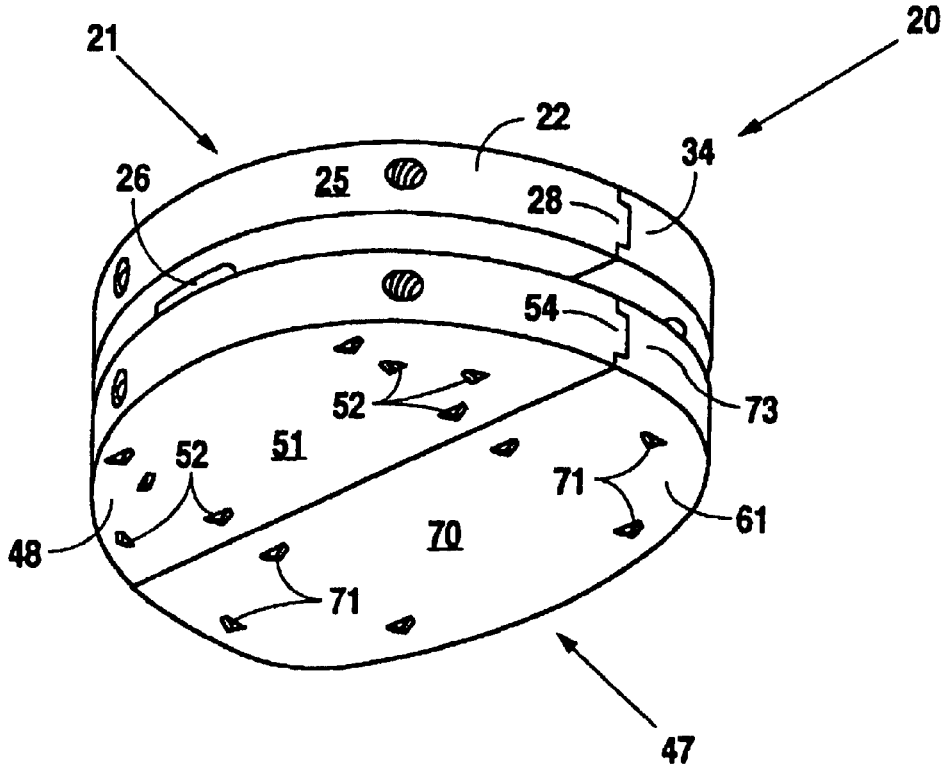
FIG. 1B shows, in an inferior perspective view, the assembled disc and facet replacement of FIG. 1.

Referring now to the figures, and to FIGS. 1A and 1B in particular, the disc and facet replacement 20 of the present invention is shown to generally comprise a substantially planar disc-shaped upper plate 21, a substantially planar disc-shaped lower plate 47 and a ball 109 interposed there between. As shown in the figures, the upper plate 21 comprises an anterior section 22 and a posterior section 34 which, as will be better understood further herein, are selectively separable one from the other to facilitate insertion into and/or removal from the intervertebral disc space 113 of a patient under treatment. Likewise, the lower plate 47 comprises an anterior section 48 and a posterior section 61, also selectively separable one from the other. As also will be better understood further herein, a plurality of section connection assemblies 79 is provided for selectively joining the anterior section 22 to the posterior section 34 of the upper plate 21 and for selectively joining the anterior section 48 to the posterior section 61 of the lower plate 47.

Figure 3:
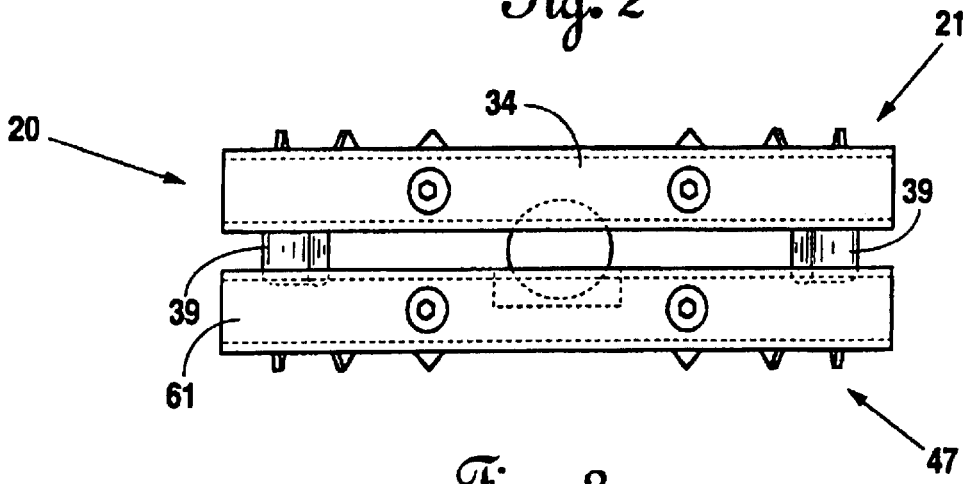
FIG. 3 shows, in a posterior elevational view, the disc and facet replacement of FIG. 1.
Figure 4:
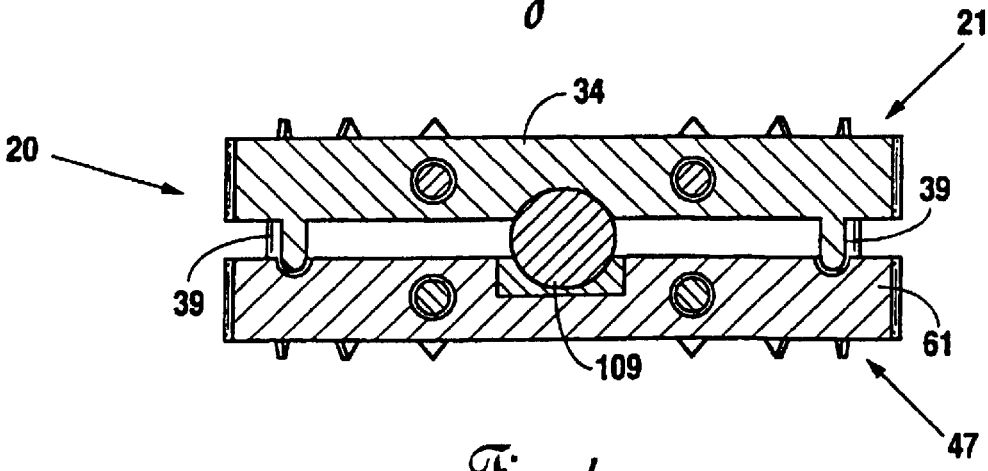
FIG. 4 shows, in a cross sectional view taken through cut line 4-4 of FIG. 2, the disc and facet replacement of FIG. 1.

As particularly shown in FIGS. 3 and 4, the lower face 25 of the anterior section 22 of the upper plate 21 is provided near its anterior edge with a preferably reniform, inferiorly projecting post 26. Similarly, the lower face 37 of the posterior section 34 of the upper plate 21 is provided about its posterior edge with a plurality of preferably reniform, inferiorly projecting post 39. Additionally, the upper face 49 of the anterior section 48 of the lower plate 47 is provided near its anterior edge with a preferably reniform slot 50 positioned to correspond to and for receiving therein the inferiorly projecting post 26 of the anterior section 22 of the upper plate 21. Still further, the upper face 62 of the posterior section 61 of the lower plate 47 is provided about its posterior edge with a plurality of preferably reniform slots 69, each slot 69 positioned to correspond to and for receiving therein one of the inferiorly projecting posts 39 of the posterior section 34 of the upper plate 21. As will be better understood further herein, the provided posts 26, 39 and slots 50, 69 cooperate with the ball 109 interposed the unitary upper plate 21 (comprising the adjoined anterior section 22 and posterior section 34) and the unitary lower plate 47 (comprising the adjoined anterior section 48 and posterior section 61) to allow limited rotation and flotation between the upper plate 21 and the lower plate 47 such that the assembled disc and facet replacement 20 very closely approximates the function of a natural three-joint disc and facet complex.

Figure 2:
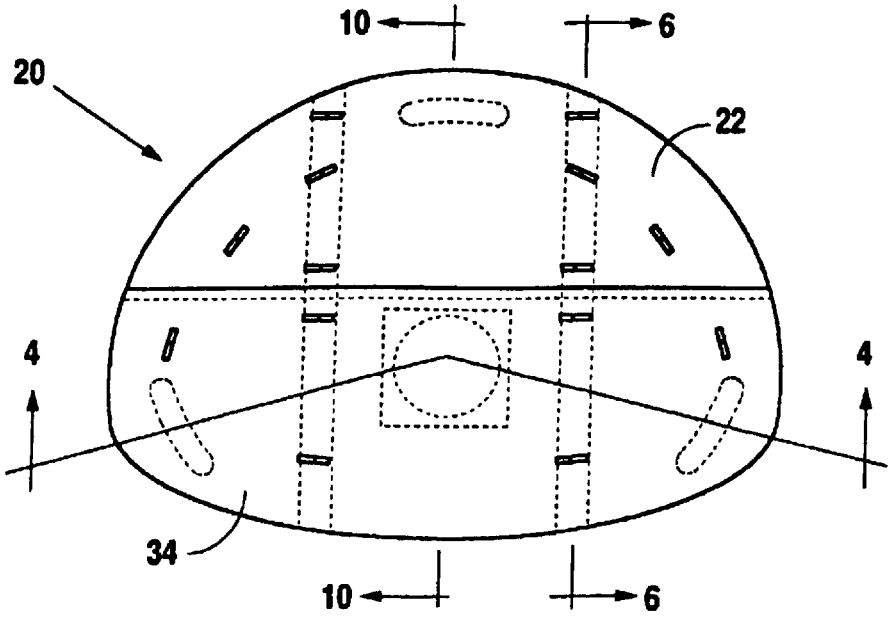
FIG. 2 shows, in a superior plan view, the disc and facet replacement of FIG. 1.
Figure 5:
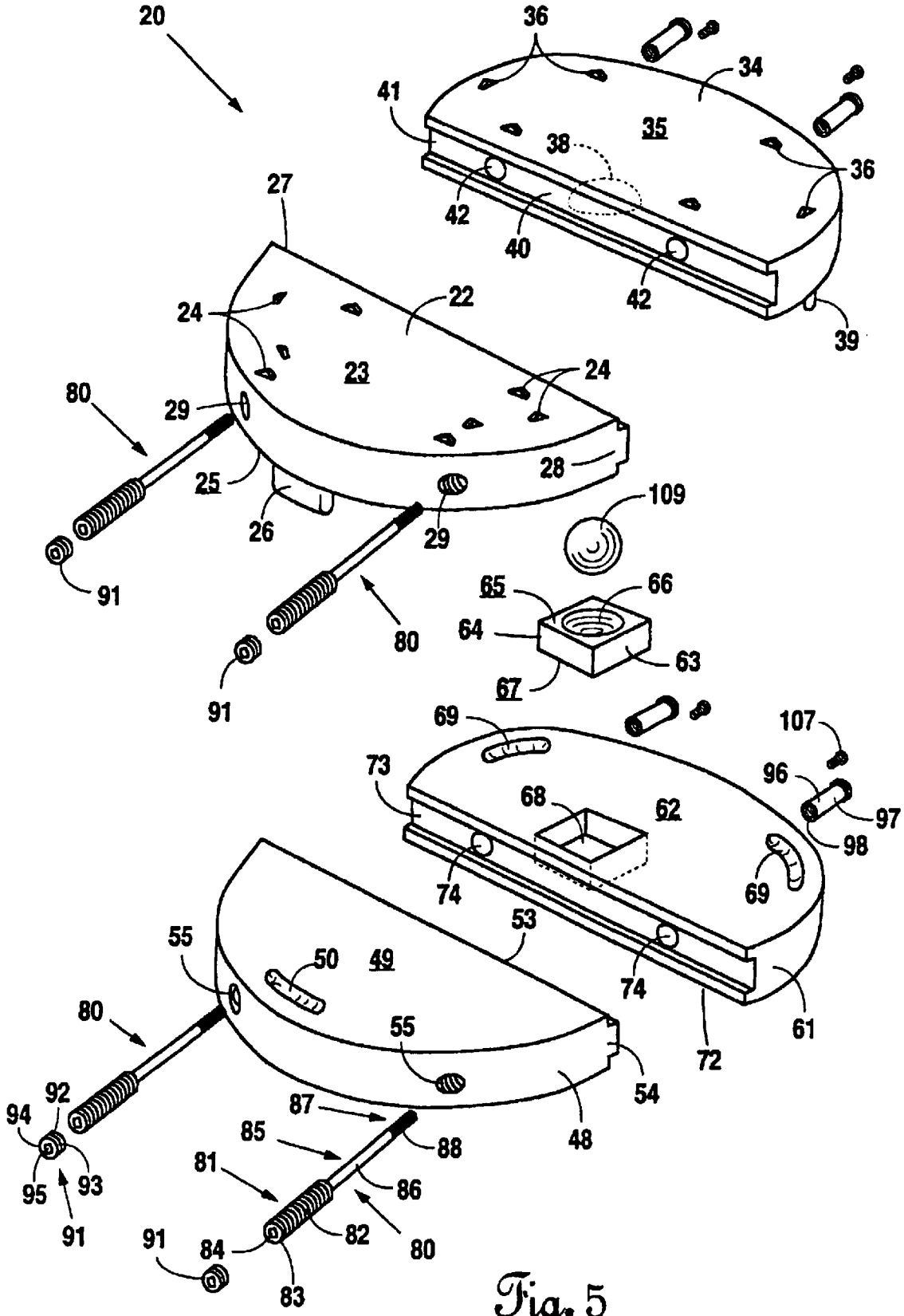
FIG. 5 shows, in a superior perspective view, the disassembled disc and facet replacement of FIG. 1.

A critical aspect of the present invention is the selective separability of the anterior section 22 and the posterior section 34 of the upper plate 21 and the selective separability of the anterior section 48 and the posterior section 61 of the lower plate 47. While not critical to the present invention, it is nonetheless highly desirable that the upper plate 21 and the lower plate 47 be provided with means for facilitating alignment of the anterior section 22 and the posterior section 34 of the upper plate 21 when joining together the anterior section 22 and the posterior section 34 to form the unitary upper plate 21 and means for facilitating alignment of the anterior section 48 and the posterior section 61 of the lower plate 47 when joining together the anterior section 48 and the posterior section 61 to form the unitary lower plate 47. To this end, as particularly shown in at least FIGS. 1, 2 and 5, the upper plate 21 and the lower plate 47 of the disc and facet replacement 20 of the present invention are provided with tongue-and-groove structures at their respective mating edges. In particular, the anterior section 22 of the upper plate 21 is shown to comprise a transversely oriented tongue 28 projecting from its posterior edge 27. Corresponding to and for receiving the provided tongue 28, a transversely oriented dado 41 is formed in the anterior edge 40 of the posterior section 34 of the upper plate 21. Likewise, a transversely oriented tongue 54 is provided on the posterior edge 53 of the anterior section 48 of the lower plate 47 and a transversely oriented dado 73, corresponding to and for receiving the tongue 54 of the lower plate 47 is provided on the anterior edge 72 of the posterior section 61 of the lower plate 47. As will be appreciated by those of ordinary skill in the art, the provided tongue-and-groove structures are very effective for both obtaining and maintaining planar alignment of the upper face 23 of the anterior section 22 of the upper plate 21 with the upper face 35 of the posterior section 34 of the upper plate 21; planar alignment of the lower face 25 of the anterior section 22 of the upper plate 21 with the lower face 37 of the posterior section 34 of the upper plate 21; planar alignment of the upper face 49 of the anterior section 48 of the lower plate 47 with the upper face 62 of the posterior section 61 of the lower plate 47; and planar alignment of the lower face 51 of the anterior section 48 of the lower plate 47 with the lower face 70 of the posterior section 61 of the lower plate 47. Although Applicant has found the described structure to be simple and effective, it should be understood that those of ordinary skill in the art will recognize that other substantially equivalent alignment obtaining and maintaining means may be provided, any and all of which should be considered within the scope of the present invention.

As previously mentioned, the selective separability of the anterior sections 22, 48 and the posterior sections 34, 61 of the upper plate 21 and the lower plate 47, respectively, is implemented in the preferred embodiment of the present invention by the provision of a plurality of section connection assemblies 79. As particularly shown in FIGS. 6 and 7, the preferred embodiment of each section connection assembly 79 comprises a specially formed connecting rod 80 adapted for insertion into and between a pair of a plurality of orifices 29, 42 or 55, 74 (provided in the upper plate 21 and lower plate 47 of the disc and facet replacement 20 and each oriented to lie substantially within both a sagittal and axial plane as detailed further herein). Additionally, each section connection assembly further comprises a specially formed sleeve 96 and a locking screw 107 adapted to cooperate with their respective connecting rod 80 and pair of provided orifices 29, 42 or 55, 74 such that the produced section connection assembly 80 may be inserted into or removed from the disc and facet replacement 20 from or to either the anterior or posterior side of the disc and facet replacement 20, thereby enabling placement or extraction of the disc and facet replacement 20 from or to either the anterior or posterior of the patient under treatment as may be medically determined to be appropriate and, in the case of extraction, without regard for whether the disc and facet replacement 20 was placed from the anterior or posterior. In this manner, the disc and facet replacement 20 represents a dramatic improvement in the art inasmuch as for the first time a surgeon is able with ease to extract a previously anteriorly placed disc replacement from the posterior, thereby avoiding the greatly increased risk of repeated anterior side surgery concomitant scarring adjacent major arteries and other major structures anterior the affected section 110 of the patient's assembled vertebrae 111. Likewise, because the disc and facet replacement 20 of the present invention is readily disassembled from either the anterior or posterior, a surgeon performing an anterior extraction of a previously posteriorly placed disc replacement may, if necessary, free and extract the disc replacement in parts as may be necessary due to bone growth about the previously placed disc replacement.

In the case of an anterior placement of the disc and facet replacement 20 of the present invention, the component parts of the disc and facet replacement 20 are assembled ex vivo prior to placement. In the case of an anterior extraction of a previously placed disc and facet replacement 20 of the present invention, the disc and facet replacement 20 may be extracted in tact or, if necessary to free it from surrounding structures, the disc and facet replacement 20 may be disassembled in situ and the components thereof removed from the intervertebral disc space 113 piecemeal. In the case of a posterior placement of the disc and facet replacement 20 of the present invention, the disc and facet replacement 20 must, in order to avoid injury to the patient's spinal cord 119 due to the limited distance that the spinal cord 119 may be extracted from within the vertebral canal 118, be placed piecemeal and assembled in situ. Likewise, in the case of a posterior extraction of a previously placed disc and facet replacement of the present invention, the disc and facet replacement 20 must be disassembled in situ and the components thereof removed from the intervertebral disc space 113 piecemeal.

Although, especially in light of this exemplary description, those of ordinary skill in the art will recognize that some steps may be performed in different order and/or differing manner, assembly ex vivo of the disc and facet replacement 20 of the present invention is generally carried out by first inserting an end plug 91 into the anterior end 56 of each of the orifices 55 of the anterior section 48 of the lower plate 47 and, likewise, inserting an end plug 91 into the anterior end 30 of each of the orifices 29 of the anterior section 22 of the upper plate 21. As particularly shown in FIGS. 6 and 7, each end plug 91 is provided about its circumference 92 with threading 93 corresponding to the interiorly threaded bore 59 of the orifices 55 of the anterior section 48 of the lower plate 47 as well as to the interiorly threaded bore 33 of each of the orifices 29 of the anterior section 22 of the upper plate 21. In order to facilitate placement or removal of the end plugs 91, each end plug 91 is provided in the center of its respective outer face 94 with an Allen, or hex, socket 95 or any other substantially equivalent drive arrangement such as, for example, a square socket, slot, or spline socket. Whatever drive arrangement is implemented, it is preferable that the provided drive arrangement does not penetrate through the respective end plug 91 in order to prevent bone growth within or infiltration of other matter into the orifices 55 through the anterior section 48 of the lower plate 47 or the orifices 29 through the anterior section 22 of the upper plate 21. If notwithstanding the foregoing potential complication, however, the end plugs 91 are nonetheless provided with sockets that penetrate completely through the end plugs 91, such sockets should be sized to prevent inadvertent engagement through the penetrating orifice formed through the end plugs 91 of tightening or loosening tools and the socket 84 provided on the anterior end 83 of the anterior section 81 of each connecting rod 80 (as described in more detail further herein). Finally, in order to permit anterior side disassembly in situ of a previously placed disc and facet replacement 20 of the present invention, it is necessary that the socket 95 of each end plug 91 be oriented to face the anterior sides of the anterior sections 22, 48.

Figure 6:
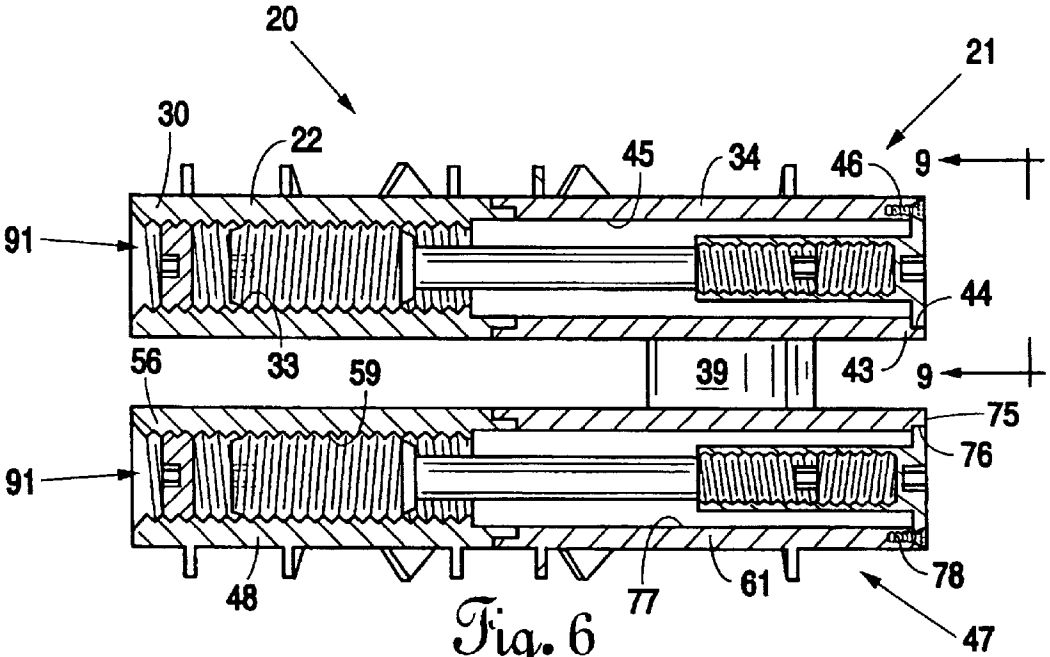
FIG. 6 shows, in a cross sectional view taken through cut line 6-6 of FIG. 2, details of the preferred embodiment of the section connection assemblies as employed for selectively joining the anterior and posterior sections each of the upper and lower plates of the disc and facet replacement of FIG. 1.
Figure 7:
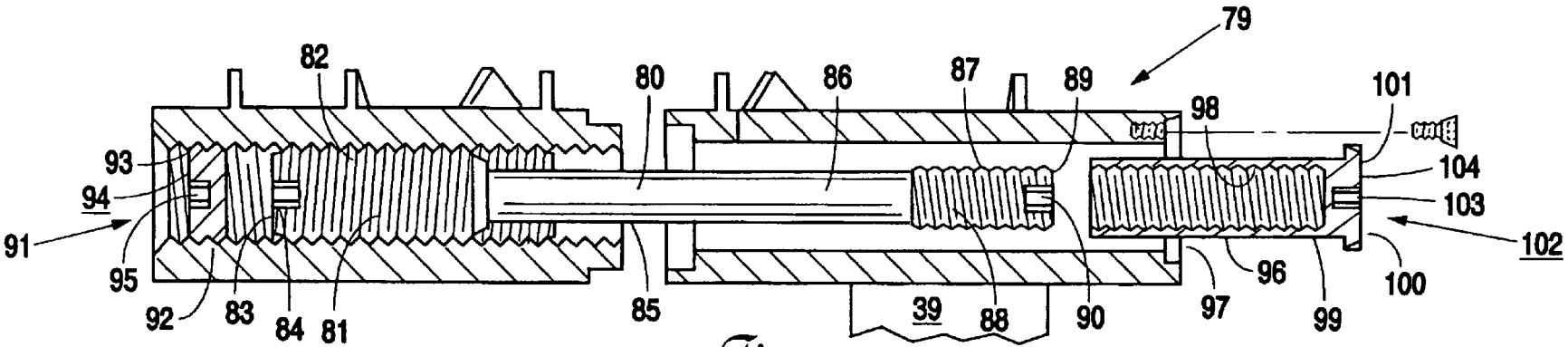
FIG. 7 shows, in an enlarged partially exploded cross sectional view corresponding to the upper portion of the view of FIG. 6, further details of a section connection assembly of the disc and facet replacement of FIG. 1.

With the end plugs 91 generally positioned as shown in FIGS. 6 and 7, assembly ex vivo of the disc and facet replacement 20 of the present invention continues by inserting the anterior section 81 of a connecting rod 80 into the posterior end of one of the orifices 55 through the anterior section 48 of the lower plate 47, whereafter the connecting rod 80 is rotated about its longitudinal axis to engage the threaded shaft 82 (conforming to the internally threaded diameter 59 of the corresponding orifice 55 through the anterior section 48 of the lower plate 47) with the interiorly threaded bore 59 of the orifice 55 through the anterior section 48 of the lower plate 47. Rotation of the connecting rod 80 is continued until the anterior section 81 of the connecting rod 80 abuts against the interior face of the previously inserted end plug 91. It is noted that the threaded shaft 82 of the anterior section 81 comprises a thread pitch reverse of that forming the threaded shaft 88 of the posterior section 87 of the connecting rod 80. Likewise, the thread pitch of the internally threaded bore 59 of the orifice 55 through the anterior section 48 of the lower plate 47 is reverse that of the internal threading 98 of the barrel 97 of each of the sleeves 96 of the section connection assemblies 79. As a result, the section connection assemblies 79 operate as turnbuckles to draw together or push apart the anterior section 48 of the lower plate 47 and the posterior section 61 of the lower plate 47. While it is necessary that opposite pitches be provided in the anterior and posterior components as discussed, it is not critical that one or the other of the anterior or posterior components be given left or right threading, the particular selection being wholly arbitrary. In any case, and as the threading is shown in the figures, the connecting rod 80 is rotated counterclockwise to effect insertion of the anterior section 81 of the connecting rod 80 fully into the orifice 55 through the anterior section 48 of the lower plate 47 and into abutment with the interior face of the end plug 91. To facilitate rotation of the connecting rods 80 in this or similar steps, each connecting rod 80 is provided on its respective posterior end 89 with an Allen, or hex, socket 90 or any other substantially equivalent drive arrangement such as, for example, a square socket, slot, or spline socket. Upon completion of this step for the first orifice 55 through the anterior section 48 of the lower plate 47, a second connecting rod 80 is inserted in identical manner into the remaining orifice 55 through the anterior section 48 of the lower plate 47.

Figure 8:
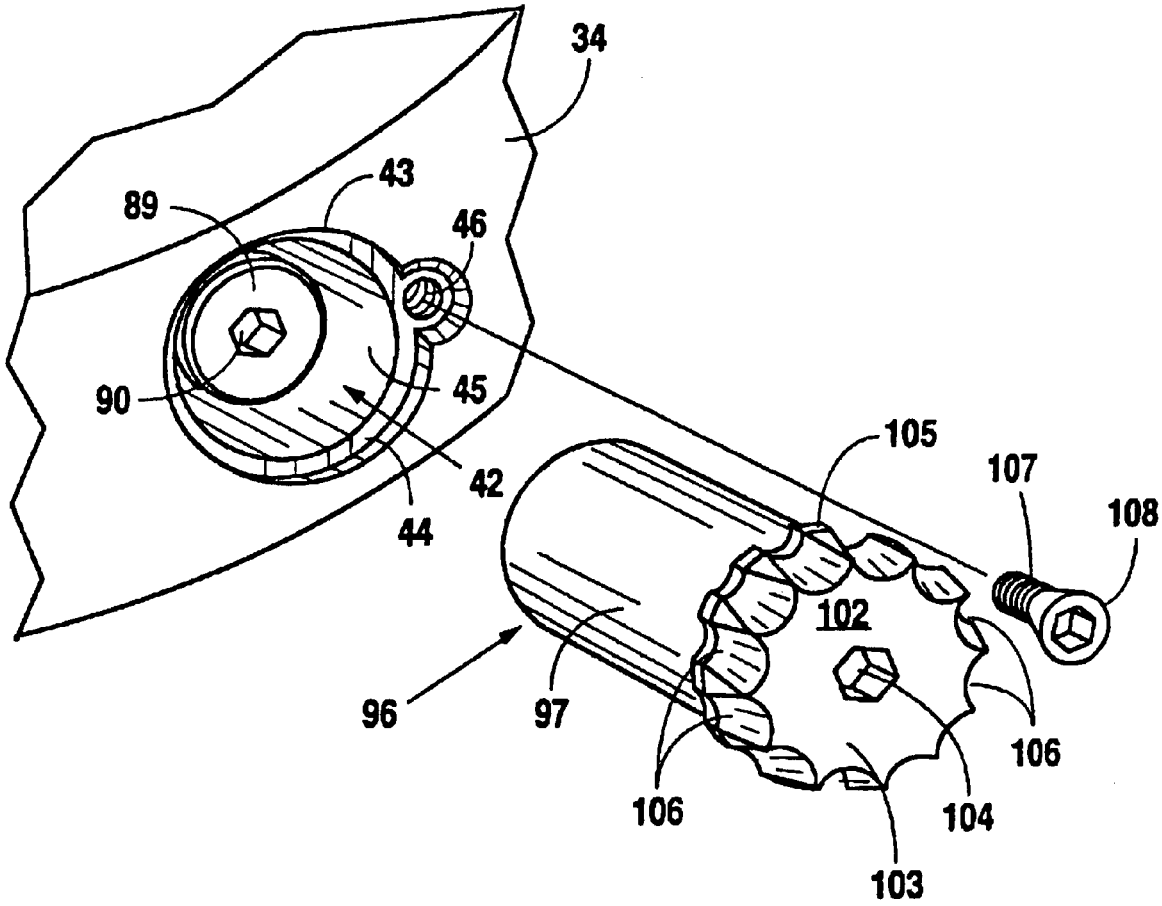
FIG. 8 shows, in a partially cut away exploded posterior perspective view, details of the anterior portion of a section connection assembly of the disc and facet replacement of FIG. 1.
Figure 9:
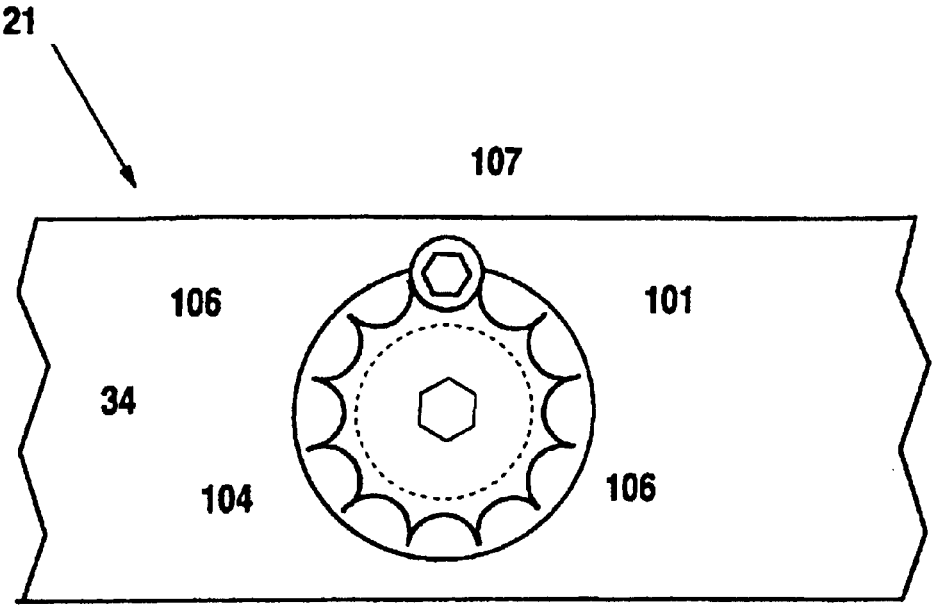
FIG. 9 shows, in an posterior plan view, various details of the section connection assembly depicted in FIG. 8 as assembled in the disc and facet replacement of FIG. 1.

With the connecting rods 80 inserted as previously described into the orifices 55 through the anterior section 48 of the lower plate 47, the anterior edge 72 of posterior section 61 of the lower plate 47 is abutted against the posterior edge 53 of the anterior section 48 of the lower plate 47, the posterior sections 87 of the connecting rods 80 being received from the anterior into the orifices 74 through the posterior section 61 of the lower plate 47. A sleeve 96 of a section connection assembly 79 is then inserted from the posterior side of the posterior section 61 of the lower plate 47 into one of the orifices 74 through the posterior section 61 of the lower plate 47. As particularly shown in FIGS. 6 through 8, the sleeves 96 of the section connection assemblies 79 each comprise a barrel 97 having internal threading 98 conforming to the diameter of the threading 88 of the posterior section 87 of the connecting rods 80 and a smooth outer circumference 99. The barrel 97 of each sleeve 96 is further sized to fit snuggly in the space between the threaded shaft 88 of the posterior section 87 of a connecting rod 80 and a smooth bore 77 forming the orifice 74 through the posterior section 61 of the lower plate. The posterior end 100 of each sleeve 96 comprises an integral cap 101, the integral cap 101 being provided in the central region of its outer face 102 with an Allen, or hex, socket 104 or any other substantially equivalent drive arrangement such as, for example, a square socket, slot, or spline socket. Utilizing the provided drive arrangement 104 (and assuming the choice of thread direction previously discussed and as shown in the figures), the sleeve 96 is rotated clockwise to engage its internal threading 98 with the threaded shaft 88 of the posterior section 87 of the respective connecting rod 80, thereby seating the integral cap 101 of the sleeve 96 into a should 76 provided about the posterior end 75 of the orifice 74 through the posterior section 61 of the lower plate 47 and drawing the posterior section 61 of the lower plate 47 tightly against the anterior section 48 of the lower plate 47. Upon completion of this step for the first orifice 74 through the posterior section 61 of the lower plate 47, a second sleeve 96 is inserted in identical manner into the remaining orifice 61 through the posterior section 61 of the lower plate 47. Finally, in order to stabilize each sleeve 96 in place, which is critical to ensure that a previously placed disc and facet replacement 20 of the present invention may if necessary be disassemble in situ from the anterior, the perimetrical region 105 of the outer face 102 of each sleeve 96 is provided with a plurality of serrations 106 sized to conform to a portion of the head of a locking screw 107 such as, for example, a flat head socket screw 108. Insertion of a locking screw 107 into each of a plurality of threaded holes 78, provided parallel to and slightly radially offset from each orifice 74 through the posterior section 61 of the lower plate 47, completes the assembly of the lower plate 47, the anterior section 48 and the posterior section 61 being completely and securely adjoined to form a unitary lower plate 47.

Temporarily setting aside the integral lower plate 47, assembly ex vivo of the disc and facet replacement 20 of the present invention continues by inserting the anterior section 81 of a connecting rod 80 into the posterior end of one of the orifices 29 through the anterior section 22 of the upper plate 21, whereafter the connecting rod 80 is rotated about its longitudinal axis to engage the threaded shaft 82 (conforming to the internally threaded diameter 33 of the corresponding orifice 29 through the anterior section 22 of the upper plate 21) with the interiorly threaded bore 33 of the orifice 29 through the anterior section 22 of the upper plate 21. Rotation of the connecting rod 80 is continued until the anterior section 81 of the connecting rod 80 abuts against the interior face of the previously inserted end plug 91. As was the case with the lower plate 47, it is noted that the threaded shaft 82 of the anterior section 81 comprises a thread pitch reverse of that forming the threaded shaft 88 of the posterior section 87 of the connecting rod 80. Likewise, the thread pitch of the internally threaded bore 33 of the orifice 29 through the anterior section 22 of the upper plate 21 is reverse that of the internal threading 98 of the barrel 97 of each of the sleeves 96 of the section connection assemblies 79. As a result, the section connection assemblies 79 operate as turnbuckles to draw together or push apart the anterior section 22 of the upper plate 21 and the posterior section 34 of the upper plate 21. While it is necessary that opposite pitches be provided in the anterior and posterior components as discussed, it is not critical that one or the other of the anterior or posterior components be given left or right threading, the particular selection being wholly arbitrary. In any case, and as the threading is shown in the figures, the connecting rod 80 is rotated counterclockwise to effect insertion of the anterior section 81 of the connecting rod 80 fully into the orifice 29 through the anterior section 22 of the upper plate 21 and into abutment with the interior face of the end plug 91. Upon completion of this step for the first orifice 29 through the anterior section 22 of the upper plate 21, a second connecting rod 80 is inserted in identical manner into the remaining orifice 29 through the anterior section 22 of the upper plate 21.

With the connecting rods 80 inserted as previously described into the orifices 29 through the anterior section 22 of the upper plate 21, the anterior edge 40 of posterior section 34 of the upper plate 21 is abutted against the posterior edge 27 of the anterior section 22 of the upper plate 21, the posterior sections 87 of the connecting rods 80 being received from the anterior into the orifices 42 through the posterior section 34 of the upper plate 21. A sleeve 96 of a section connection assembly 79 is then inserted from the posterior side of the posterior section 34 of the upper plate 21 into one of the orifices 42 through the posterior section 34 of the upper plate 21. As was the case with the lower plate 47, the barrel 97 of each sleeve 96 is sized to fit snuggly in the space between the threaded shaft 88 of the posterior section 87 of a connecting rod 80 and a smooth bore 45 forming the orifice 42 through the posterior section 34 of the upper plate 21. Utilizing the provided drive arrangement 104 as previously described (and assuming the choice of thread direction previously discussed and as shown in the figures), the sleeve 96 is rotated clockwise to engage its internal threading 98 with the threaded shaft 88 of the posterior section 87 of the respective connecting rod 80, thereby seating the integral cap 101 of the sleeve 96 into a shoulder 44 provided about the posterior end 43 of the orifice 42 through the posterior section 34 of the upper plate 21 and drawing the posterior section 34 of the upper plate 21 tightly against the anterior section 22 of the upper plate 21. Upon completion of this step for the first orifice 42 through the posterior section 42 of the upper plate 21, a second sleeve 96 is inserted in identical manner into the remaining orifice 42 through the posterior section 34 of the upper plate 21. Finally, in order to stabilize each sleeve 96 in place, a locking screw 107 is inserted into each of a plurality of threaded holes 46 provided parallel to and slightly radially offset from each orifice 42 through the posterior section 34 of the upper plate 21, thereby completing the assembly of the upper plate 21, the anterior section 22 and the posterior section 34 being completely and securely adjoined to form a unitary upper plate 21.

Figure 10:
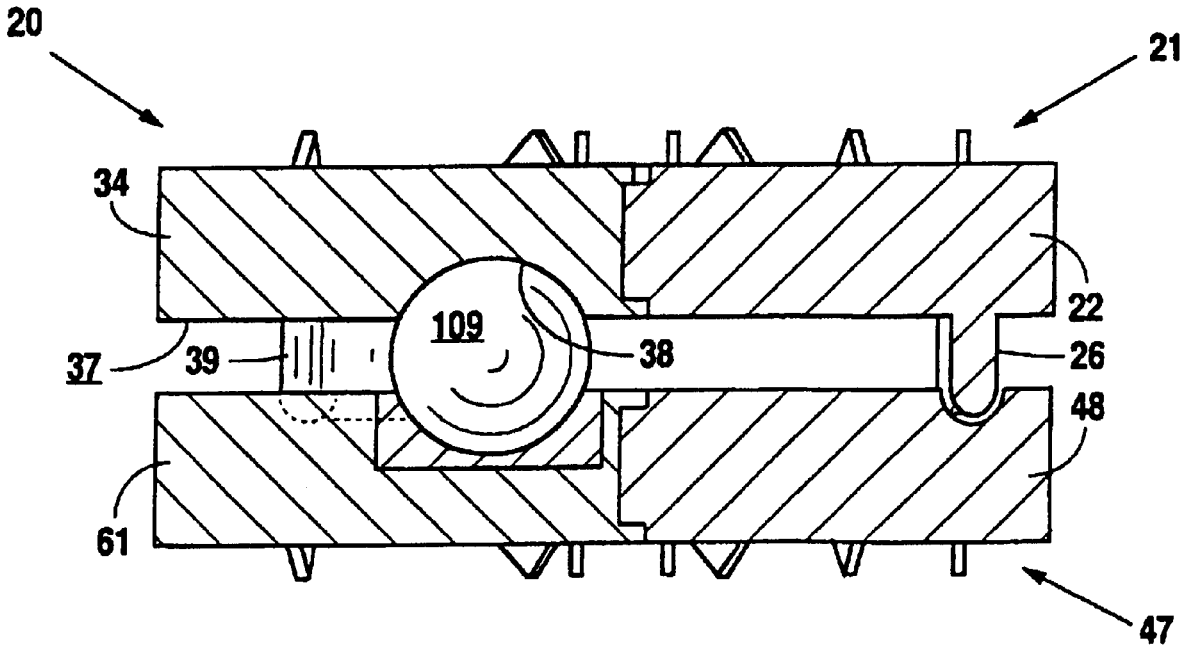
FIG. 10 shows, in a cross sectional view taken through cut line 10-10 of FIG. 2, details of a first preferred placement between the upper and lower plates of the ball of the disc and facet replacement of FIG. 1.

As previously discussed, the provided posts 26, 39 and slots 50, 69 cooperate with the ball 109 interposed the unitary upper plate 21 and the unitary lower plate 47 to allow limited rotation and flotation between the upper plate 21 and the lower plate 47 such that the assembled disc and facet replacement 20 very closely approximates the function of a natural three-joint disc and facet complex. In a first preferred embodiment of the present invention as particularly shown in FIGS. 5 and 10, a defect 68, having a standardized footprint, is provided on the upper face 62 of the posterior section 61 of the lower plate 47. In this embodiment, an insert 63 having a perimeter 64 sized to fit into the standardized footprint of the defect 68 and having a socket 66 (corresponding in size to the ball 109) on its upper face 65 is also provided. In this manner, the surgeon placing the disc and facet replacement 20 of the present invention may select from a plurality of differing height inserts 63 to accommodate during the actual surgical procedure for the actual superior-inferior dimension of the intervertebral disc space 113 of a particular patient. In particular, the surgeon may measure the dimension, select an appropriate one of the inserts 63 and place the lower face 67 of the insert 63 into the defect 68. The ball 109 may then be positioned between the socket 66 on the upper face 65 of the selected and placed insert 63 and a corresponding socket 38 (also corresponding in size to the ball 109) provided on the lower face 37 of the posterior section 34 of the upper plate 21.

Figure 14:
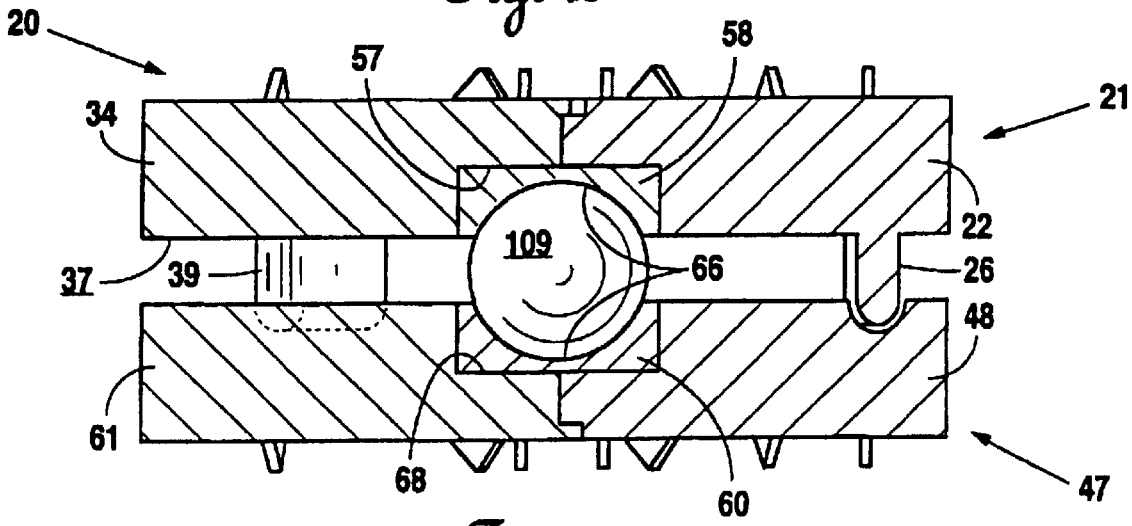
FIG. 14 shows, in a cross sectional view generally corresponding to the view of FIG. 10, details of the alternative implementation depicted in FIG. 13.
Figure 13:
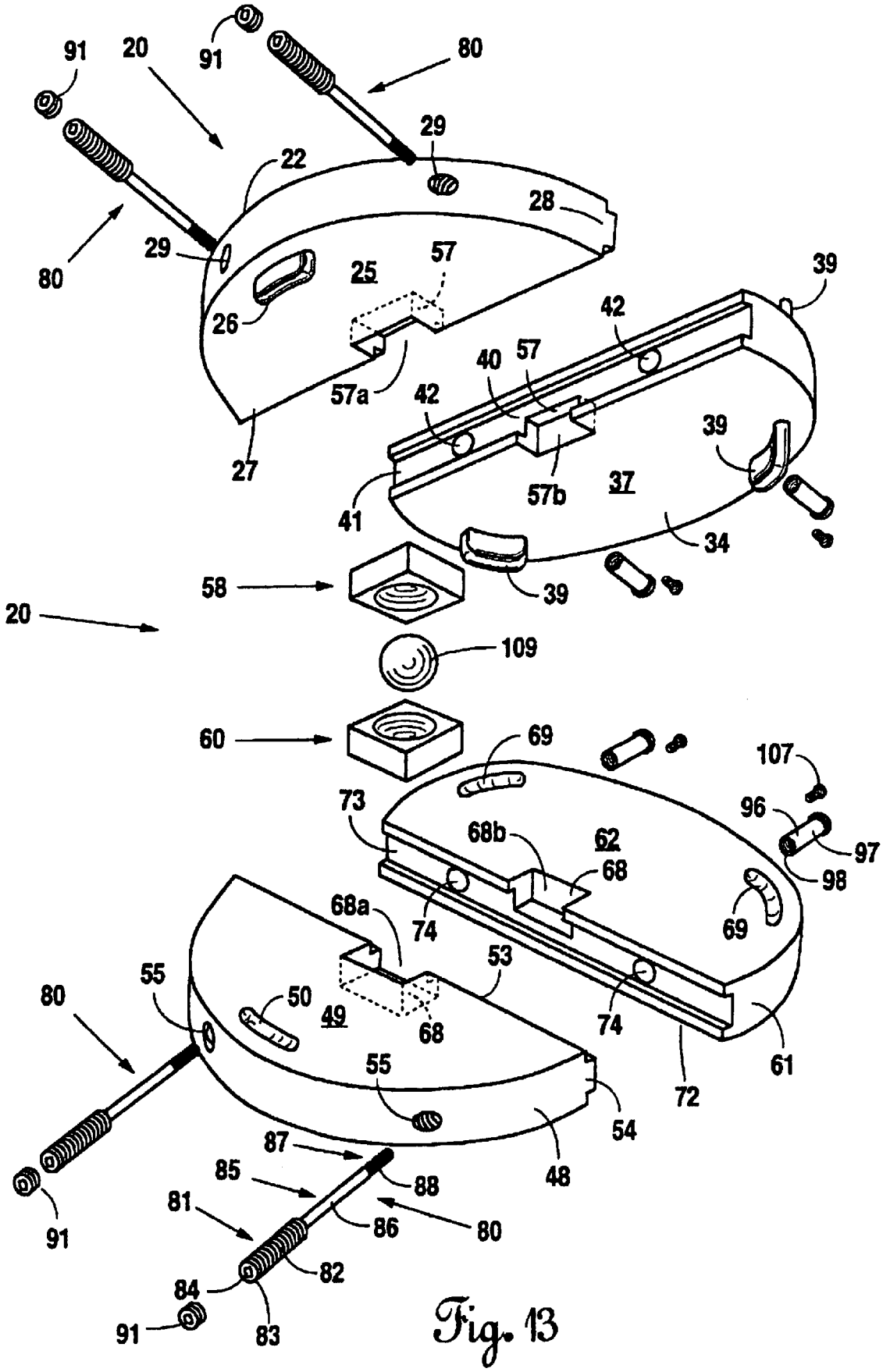
FIG. 13 shows, in a side perspective view, the disassembled disc and facet replacement of the present invention as implemented with an alternative preferred placement between the upper and lower plates of the ball.

In a second preferred embodiment of the present invention as particularly shown in FIGS. 13 and 14, such a defect 57 may also be provided in the upper plate 21 with a corresponding upper plate insert 58. Additionally, as also shown in FIGS. 13 and 14, either or both of the defects 57, 68 may be positioned across the adjoining edges 27, 40 of the anterior section 22 and posterior section 34, respectively, of the upper plate 21 and/or across the adjoining edges 53, 72 of the anterior section 48 and posterior section 61, respectively, of the lower plate 47. In this case, the upper plate defect 57 will comprise an anterior portion 57*a* formed in the lower face 25 of the anterior section 22 of the upper plate 21 and a posterior portion 57*b* formed in the lower face 37 of the posterior section 34 of the upper plate 21. Likewise, the lower plate defect 68 will comprise an anterior portion 68*a* formed in the upper face 49 of the anterior section 48 of the lower plate 47 and a posterior section 68*b* formed in the upper face 62 of the posterior section 61 of the lower plate 47. In any case, it should be understood that all combinations of usages of the foregoing described aspects are contemplated within the scope of the present invention, any particular implementation being dependent only upon the particular dynamics of the surgical case.

With the ball 109 sandwiched in place between the unitary upper plate 21 and the unitary lower plate 47 with or without implementation of one or both of the inserts 58, 60, the disc and facet replacement 20 as assembled ex vivo is fully prepared for anterior side placement into the intervertebral disc space 113 of a patient under treatment. The surgeon need only first prepare the intervertebral disc space 113 by surgically removing the affected intervertebral disc 114 from between the superior and inferior vertebral bodies 112.

Figure 11:
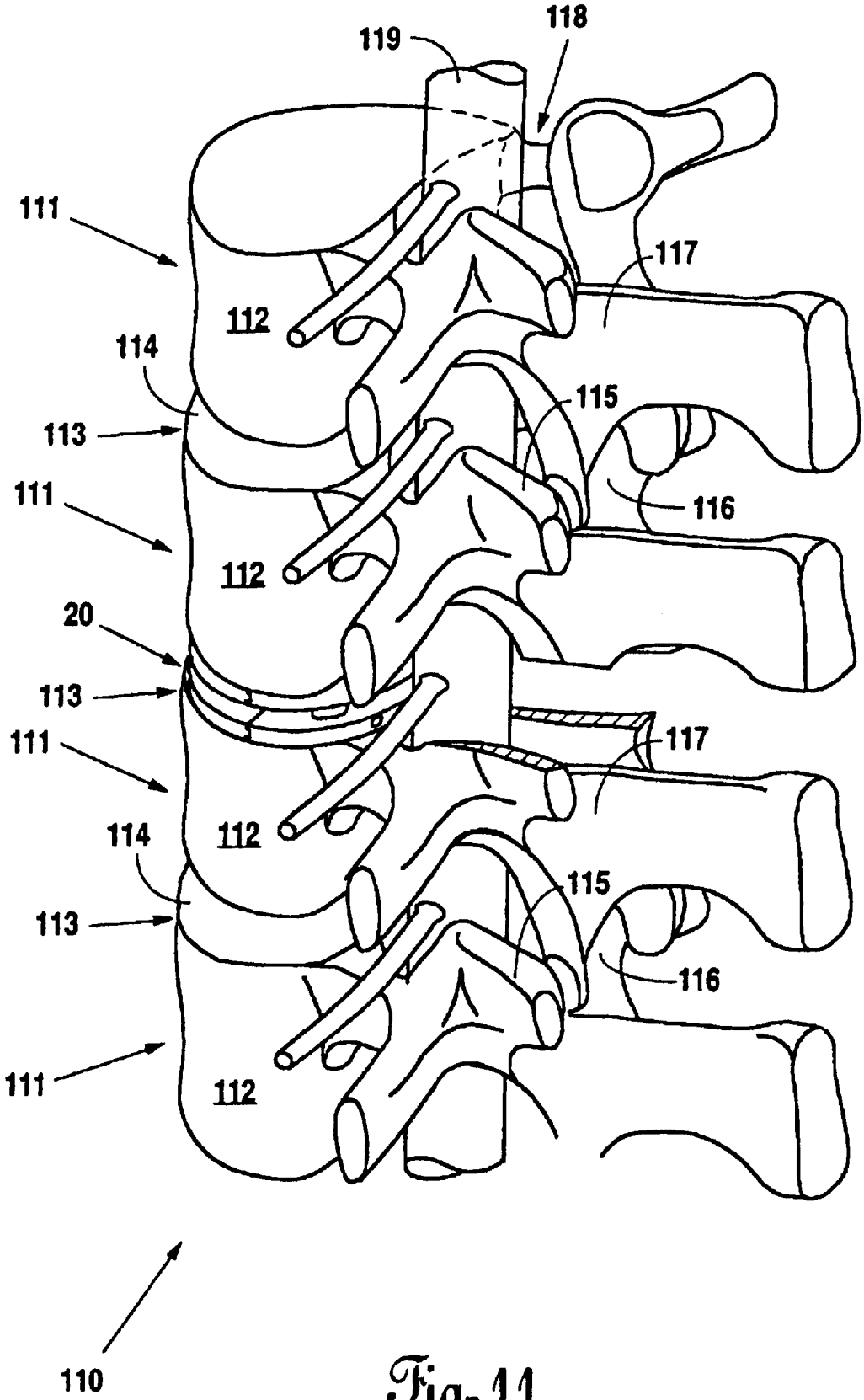
FIG. 11 shows, in a superior-posterior perspective view of assembled vertebrae, the disc and facet replacement of FIG. 1 as surgically placed within a previously prepared intervertebral disc space.
Figure 12:
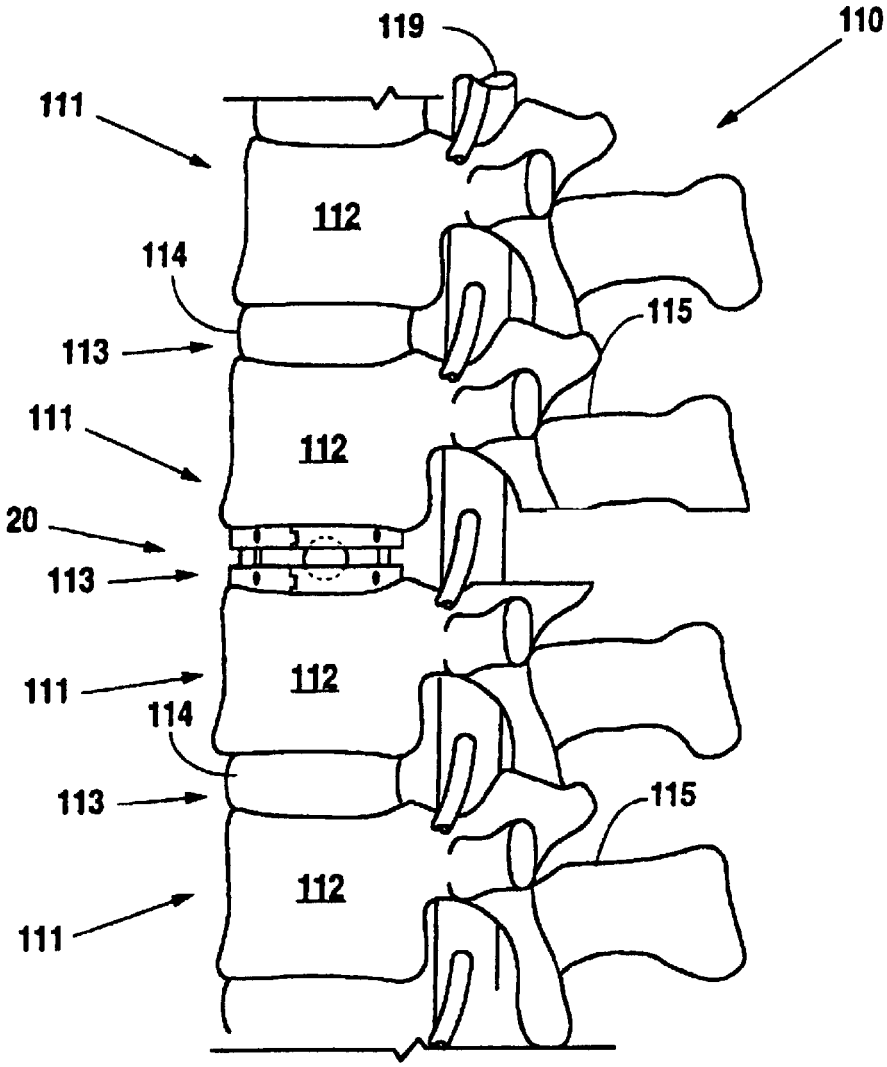
FIG. 12 shows, in a side elevational view, the placement of FIG. 11.

Assembly in situ for a posterior insertion of the disc and facet replacement 20 of the present invention is preceded by preparation of the surgical site by first excising portions of the superior articular process 115 from the inferior vertebra and portions of the inferior articular process 116 and lamina 117 from the superior vertebra as necessary to access the intervertebral disc space 113 as shown in FIGS. 11 and 12. Assembly in situ then takes place as described ex vivo with the exception that the constituent parts are laid in place in the intervertebral disc space 113 as assembly takes place. In particular, the anterior section 48 of the lower plate 47 is placed (with end plugs 91 inserted and positioned); the connecting rods 80 are inserted (being placed about the sides of the patient's spinal cord 119); the posterior section 61 of the lower plate 47 is placed; and then the sleeves 96 are affixed and locked. The lower plate insert 60, if utilized, is then placed in the lower plate defect 68 and the ball 109 is placed. Finally, the upper plate 21 is likewise placed and assembled. For posterior side extraction of the disc and facet replacement 20 of the present invention the disc and facet replacement 20 must be disassembled in situ following the previously described procedure in reverse order.

Finally, as previously discussed, the present invention contemplates that it may under some circumstances be necessary to disassemble in situ a previously placed disc and facet replacement 20 for removal of the disc and facet replacement 20 from the anterior side. In this case (still assuming the threading adopted previously herein), the disc and facet replacement 20 is disassembled by first removing the end plugs 91 by clockwise rotation. The connecting rods 80 are then removed to the anterior by clockwise rotation of the rods 80 from their respective anterior ends 83 until the anterior sections 22, 28 pull away and separate from their respective posterior sections 34, 61. Upon separation, the component parts of the disc and facet replacement 20 may be extracted piecemeal.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. For example, stabilizing spikes 24, 36, 52, 71 may be provided on the outer faces 23, 35, 51, 70 of the disc and facet replacement 20 to promote stability of the disc and facet replacement 20 post-placement. Additionally, those of ordinary skill in the art will recognize that the midsection 85 of the connecting rods 80 may comprise a smooth shaft 86 in order to limit threading about the rods 80 as may be necessary to ensure separation of the anterior sections 22, 28 and posterior sections 34, 61 during disassembly of the disc and facet replacement 20. Still further, those of ordinary skill in the art will recognize that while the present invention is preferably constructed of polyetheretherketone other materials such carbon fiber, titanium or any substantial equivalent of any of these materials may be utilized. In any case, because the scope of the present invention is much broader than any particular embodiment, the foregoing detailed description should not be construed as a limitation of the scope of the present invention, which is limited only by the claims appended hereto.

What is claimed is:

1. An artificial disc for replacement of a spinal three-joint complex of a mammal, said artificial disc comprising:

a generally spinal disc-shaped upper plate comprising an anterior section and a posterior section, said anterior section of said upper plate being selectively separable from said posterior section of said upper plate;

a generally spinal disc-shaped lower plate comprising an anterior section and a posterior section, said anterior section of said lower plate being selectively separable from said posterior section of said lower plate;

a ball interposed a lower face of said upper plate and an upper face of said lower plate;

a plurality of posts, each said post projecting from one of said faces toward the other of said faces; and a plurality of detents for engaging said posts, each said detent corresponding to one of said posts and being provided on the one of said faces opposite the face from which said corresponding post projects.

2. The artificial disc as recited in claim 1, wherein:

at least one said post projects from said lower face of said upper plate; and at least one said detent, corresponding to said post projecting from said lower face of said upper plate, is provided on said upper face of said lower plate and positioned opposite said post projecting from said lower face of said upper plate.

3. The artificial disc as recited in claim 2, wherein:

each said post projects from said lower face of said upper plate; and each said detent, corresponding to one of said posts, is provided on said upper face of said lower plate and positioned opposite said corresponding post.

4. The artificial disc as recited in claim 1, wherein:

at least one said post projects from said upper face of said lower plate; and at least one said detent, corresponding to said post projecting from said upper face of said lower plate, is provided on said lower face of said upper plate and positioned opposite said post projecting from said upper face of said lower plate.

5. The artificial disc as recited in claim 4, wherein:

each said post projects from said upper face of said lower plate; and each said detent, corresponding to one of said posts, is provided on said lower face of said upper plate and positioned opposite said corresponding post.

6. The artificial disc as recited in claim 1, wherein each said post comprises a generally reniform cross section.

7. The artificial disc as recited in claim 6, wherein each said detent comprises a generally reniform perimeter.

8. The artificial disc as recited in claim 1, wherein each said detent comprises a generally reniform perimeter.

9. The artificial disc as recited in claim 1, wherein said anterior section and said posterior section of each said plate is interconnected one to the other with a section connection assembly, each said section connection assembly comprising a connecting rod inserted into and between said anterior section and said posterior section and oriented to lie substantially within both a sagittal plane and an axial plane.

10. The artificial disc as recited in claim 9, wherein each said anterior section of said plates comprises a first bore for receiving therein an anterior section of one of said connecting rods and each said posterior section of said plates comprises a second bore for receiving therein a posterior section of one of said connecting rods.

* * * * *